United States Patent [19]

Snooks

[11] 4,328,056

[45] May 4, 1982

[54] METHOD OF MAKING A CUFFED TUBE

[75] Inventor: Gregory L. Snooks, Creve Coeur, Mo.

[73] Assignee: Sherwood Medical Industries Inc., St. Louis, Mo.

[21] Appl. No.: 167,073

[22] Filed: Jul. 9, 1980

[51] Int. Cl.[3] ..................... A61M 25/00; B29B 11/00; B29D 23/04

[52] U.S. Cl. ................................ 156/242; 128/349 B; 156/244.13; 156/245; 156/293

[58] Field of Search ........... 156/242, 245, 293, 244.13; 128/349 B; 264/248, 259

[56] References Cited

U.S. PATENT DOCUMENTS 2,849,001 8/1958 Oddo ............................... 128/349 B
3,173,418 3/1965 Baran ............................... 128/349 B
3,459,175 8/1969 Miller ............................... 128/349 B
3,481,339 12/1969 Millet ............................... 128/349 B

*Primary Examiner*—Caleb Weston
*Attorney, Agent, or Firm*—S. N. Garber; W. R. O'Meara

[57] ABSTRACT

A method of making a double-cuffed endotracheal tube is disclosed which includes forming a unitary double-cuff member, inserting and inverting one of the cuffs into the other cuff and connecting the cuffs on a plastic tube, and sealingly connecting the ends of the cuffs to the tube. A method of sealingly connecting one end of the inner cuff which is within the outer cuff to the tube includes inserting a pipe into the tube and through a sidewall opening in the tube, and flowing sealant material through the tube to seal one end of the inner cuff to the tube.

20 Claims, 3 Drawing Figures

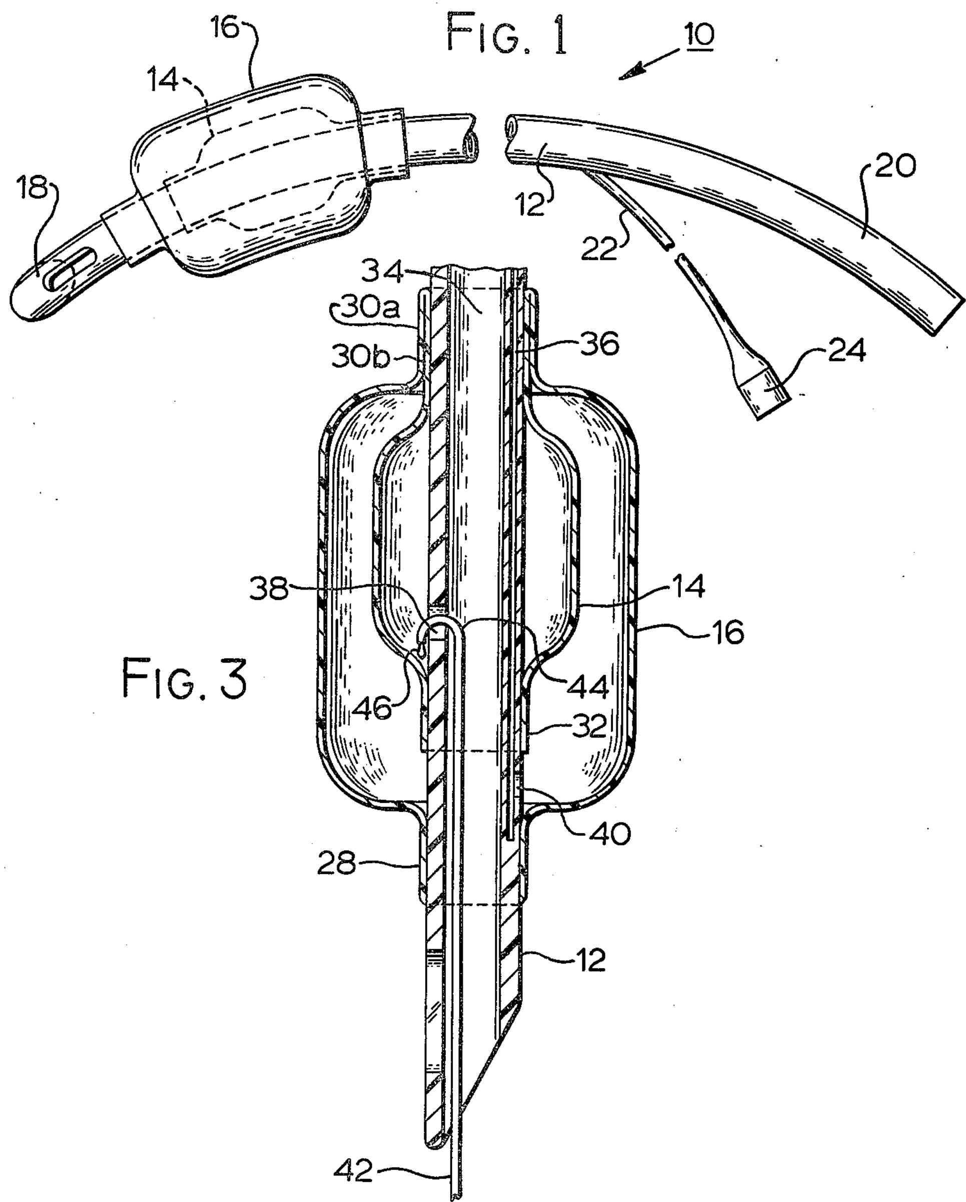
FIG. 1
10
16
14
18
12
20
22
24
34
30a
30b
36
38
14
16
FIG. 3
46
44
32
40
28
12
42
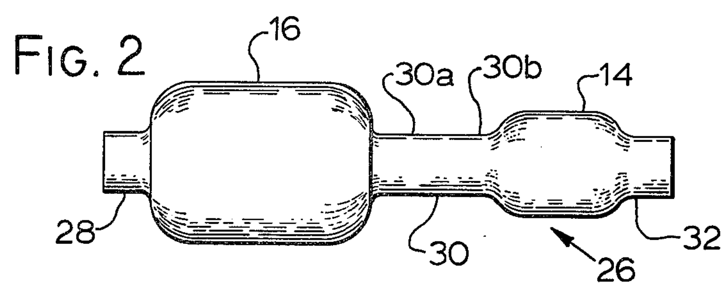
FIG. 2
16
30a
30b
14
28
30
26
32

METHOD OF MAKING A CUFFED TUBE

DESCRIPTION

1. Technical Field

This invention relates to a method of making a cuffed tube and more particularly to a method of making a double-cuffed retention tube.

2. Background Art

Single-cuff retention tubes, such as endotracheal tubes, are commonly used for artificial respiration of the unconscious or anesthetized patient. The cuff is generally pressurized sufficiently to provide a seal between the tube and the tracheal wall and to prevent inadvertant extubation during the respiration cycle. As is well known, damage to the tracheal walls can occur because of relatively high cuff pressures during prolonged use. Double-cuffed endotracheal tubes have been proposed in order to reduce injury to the trachea. It has been proposed to position a second smaller cuff within the main sealing cuff and connect the inner cuff with the ventilation lumen of the tube. In this way, the outer sealing cuff can be pressurized to a relatively low pressure or a pressure just necessary to provide a seal with the tracheal wall and hold the tube in place at times when minimum pressure is acting on the lungs. As the pressure in the lungs increases and decreases during the respiration cycle, the pressure inside the inner cuff will vary and, in turn, vary the pressure in the outer sealing cuff. In this way, pressures applied by the sealing cuff against the membranes of the trachea will vary in accordance with the pressures needed during the respiration cycle and the chance of injury to the trachea is reduced since high pressures are not continuously applied to the trachea. U.S. Pat. No. 3,481,339, for example, discloses a double-cuffed endotracheal tube.

Such double-cuffed endotracheal tubes, however, are relatively difficult and expensive to manufacture. For example, a separate molding operation for each of the two cuffs is generally used. Also, in assembling the cuffs, each cuff has to be predeterminately positioned on the tube and sealingly connected to the tube, and this requires tedious and time consuming operations that increase the cost.

DISCLOSURE OF THE INVENTION

An object of the present invention is to provide an improved method of making a double-cuffed retention tube which is relatively simple and economical, and which in general, substantially overcomes the above problems. This is accomplished in accordance with one aspect of the present invention by forming a pair of integrally connected cuffs, inverting one of the cuffs and inserting it into the other cuff, and securing the ends of the cuffs in a desired location on a tube. In accordance with another aspect of the invention, one cuff is positioned within another cuff on a tube, and the ends of the cuffs are sealingly connected to the tube. An end of the inner cuff is sealingly connected by inserting a pipe into the tube with one end of the pipe extending through a sidewall opening in the tube, and then flowing a sealant material through the pipe to seal the one end of the inner cuff to the tube.

These, as well as other objects and advantages of the present invention, will become apparent from the following detailed instruction and accompanying drawing.

BRIEF DESCRIPTION OF THE DRAWING

FIG. 1 is a side view of a double-cuffed endotracheal tube made in accordance with a preferred method of the invention;

FIG. 2 is a side view illustrating a double-cuffed member used in making the endotracheal tube of FIG. 1; and FIG. 3 is an enlarged side cross-sectional view, rotated 90°, of the distal end portion of the endotracheal tube of FIG. 1 and illustrating a method of positioning and sealing the double-cuff member of FIG. 2 onto the tube of FIG. 1.

DETAILED DESCRIPTION OF THE INVENTION

Referring now to the drawing, and particularly to FIG. 1, a double-cuffed endotracheal tube 10 is shown including a plastic tube 12 having a pair of inner and outer balloon cuffs 14 and 16 disposed on tube 12 adjacent the distal end 18 of the tube. The proximal end 20 of tube 12 is adapted to be connected to a respirator. A tube 22 having a suitable or conventional one-way valve 24 is connected to tube 12 for inflating the outer cuff 16, as will be discussed hereafter.

In making the endotracheal tube 12, cuffs 14 or 16 are postformed, preferably, both cuffs are integrally formed at the same time or in the same process to produce a unitary double-cuff member indicated generally at 26 in FIG. 2. The double cuff member 26 includes a generally cylindrical cuff connector portion 28 at one end of the member which is connected to one end of the cuff 16, a generally cylindrical center cuff connector portion 30 integrally connected between the opposite end of cuff 16 and one end of cuff 14, and a proximal end generally cylindrical cuff connector portion 32 connected to the opposite end of cuff 14. The generally cylindrical or tubular connector portions 28, 30 and 32 of member 26 are formed such that they have an inner diameter approximately equal to the outer diameter of tube 12, and preferably, slightly less than the outer diameter of the tube to provide a snug fit with the tube.

The double cuff member 26 may be formed of any suitable cuff material such as a suitable plastic and may be made of supple elastic or substantially non-elastic plastic or rubber, for example, silicone rubber, polyvinyl chloride, polyurethane or other plastic may be used to form member 26. The cuffs are formed so that they are inflatable and deflatable when gas pressurized and depressurized. The member 26 may be made by various well known manufacturing methods such as dip forming, blow molding, extrusion molding, injection blow molding or other methods. The cuffs 14 and 16 are preferably made from the same mold and/or the same parison.

The tube 12 may be conventionally extruded from any suitable tube or catheter plastic material, for example, a natural or synthetic rubber or thermoplastic material such as polyvinyl chloride may be used. As seen in FIG. 3, the tube 12 has a main or ventilation lumen 34 extending entirely through the tube, and a relatively smaller auxiliary lumen 36 formed in the sidewall of the tube which is closed at the distal end and connected at the proximal end with the inflation tube 22 and one-way valve 24 (FIG. 1). The tube 12 has at least one opening 38 through the sidewall which connects the inner cuff 14 in fluid communication with the main lumen 34. At least one opening 40 through the outer sidewall of the auxiliary lumen 36 connects the outer cuff 16 in fluid communication with the auxiliary lumen and the inflation tube 22. Instead of extruding tube 12 with an auxillary lumen in the sidewall, an auxiliary lumen can be provided by attaching a separate tube to tube 12.

The inner cuff 14 is made smaller than the outer cuff 16. The size of the small cuff is chosen such that, when it is fully inflated, and when maximum pressure is applied to the lungs the predeterminately pressurized outer cuff 16 will apply a desired maximum pressure to the trachea walls for sealingly holding the tube in place. When the inner cuff 14 is fully deflated or collapsed the outer cuff pressure is reduced to its minimum predetermined pressure which holds the tube in place during periods of low lung pressure. In the drawing, the cuffs are shown for illustration in their inflated condition for sake of clarity.

The unitary cuff member 26 containing the inner and outer cuffs 14 and 16 is applied to tube 12 by inverting and moving the cuff 14 into the interior of the outer 16 and then pulling the telescoped cuffs onto the end of the catheter or holding the telescoped cuffs and inserting the tube 12 into the cuffs. During the insertion of cuff 14 into cuff 16, the cuff 14 is inverted or turned inside-out (FIG. 3) and the cylindrical cuff portion 30 (FIG. 2) between the cuffs becomes folded back upon itself providing concentric proximal cylindrical cuff portions 30*a* and 30*b*. The outer surfaces of cuff 14 and cylindrical cuff portions 30*b* and 32, as viewed in FIG. 2, are on the inside or become radially inner surfaces when the cuffs are on the tube as shown in FIG. 3. The cuffs 14 and 16 are positioned on tube 12 so that the opening 38 is within the inner cuff 14 and the opening 40 is within the outer cuff 16. The cuff portion 32 is shown wholly within cuff 16 and spaced proximally of portion 28.

The proximal ends of cuffs 14 and 16, portions 30*a* and 30*b*, and the distal end of cuff 16, portion 28, are sealingly secured to the outer surface of tube 12 by any suitable or conventional means. For example, a suitable securing sealant material such as a tube material solvent or adhesive may be inserted between the cuff portion 30*b* and the tube 12, and between the inner surface of cuff portion 28 and the outer surface of tube 12 from the exterior of the tube. In some cases, induction heating may be employed to raise the temperatures of the plastic to a temperature sufficient to cause adhesion between the cuff portions 28 and 30*b* and tube 12.

In order to sealingly secure the distal end or portion 32 of cuff 14 to the tube 12, a sealant, such as a suitable medical grade adhesive or a solvent is applied between to the inner surface of the connector portion 32 and outer surface of tube 12 to effect an adhesive connection between the distal end of cuff 14 and the tube 12. Where the tube 12 and cuffs 14 and 16 are made of polyvinyl chloride, a solvent such as cyclohexanone provides a good solvent bond between the cuff and the tube. As is shown in FIG. 3, a hollow needle or tube 42 of small diameter is inserted into the distal end of tube lumen 34 to apply the sealant, such as the above solvent, to the facing surfaces of the cylindrical portion 32 of cuffs 14 and the tube 12. The needle 42 may be connected at one end with a source of the solvent or cement which can be pressurized. The tip of the inserted end of the needle 42 is U-shaped or curved back upon itself. The tip end of the needle 42 is indicated at 44 and is curved so that the tip can enter and pass through hole 38 in the sidewall of the tube 12 and be adjacent to the distal end of the cuff 14 or cuff portion 32 for applying a sufficient amount of solvent. A drop of such sealant is shown for illustration at 46 in FIG. 3. The applied solvent is ejected from the needle 42 and distributes itself evenly as a result of surface tension so as to provide a good sealing connection between the distal end portion 32 of cuff 14 and the tube 12. The needle 14 is then removed from hole 38 and the main lumen 34.

Where desired, cement or solvent may be applied between the facing surfaces of the cylindrical cuff portions 30*a* and 30*b* just prior to inserting cuff 14 into cuff 16.

Since both cuffs can be made integrally from the same parison or mold, such a single operation reduces costs. Also, since the two cuffs 14 and 16 can be formed and applied to tube 12 while integrally connected, the location of the one cuff relative to the other cuff and to the tube 12 is substantially automatically and simultaneously obtained when one cuff is located after the cuffs are telescoped. This avoids the problem of positioning separate cuffs relative to each other and to the tube as in the past.

The method of sealingly connecting the distal end or cuff portion 32 to the tube could also be employed where discrete or separate concentric cuffs are employed. Also, in some cases, the outer cuff portion 28 may be pulled proximally enough to permit insertion of a sealant material between portion 32 and the tube 12 from outside the device 10. In some cases, it is possible to position the folded-back portion 30 at the distal end of tube 12 with the portion 28 proximally of the portion 30.

In use, the double-cuff 14, 16, is disposed in the throat. The outer cuff may be inflated to a relatively low pressure and the distal end 20 of tube 12 connected to a respiration system that applies intermittent positive gas pressures to the main lumen and lungs of the patient to thereby effect lung ventilation. As gas or air pressure increases in the lungs the inner cuff 14 inflates thereby increasing the sealing pressure applied to the trachea walls by the outer cuff 16. As the lung pressure decreases, the inner cuff 14 deflates thereby reducing the pressure applied to the trachea walls by the outer cuff 16. This cycle continues during respiration so that the relatively high pressure applied to the trachea walls is intermittent instead of continuous.

Where a separate inflation tube having a separate inflation lumen is used instead of the integral auxiliary lumen 36, the separate inflation tube can extend along the outer or inner surface of the tube 12 and be connected directly to the outer cuff 16.

As various changes may be made in the above described construction and method without departing from the scope of the invention, it is intended that all matter contained in the above description and shown in the accompanying drawing be interpreted as illustrative and not in a limiting sense.

I claim:

1. A method of making a medical double-cuffed retention tube for insertion and retention in a body cavity comprising the steps of providing a tube having a main lumen therethrough and auxiliary lumen means, forming a pair of inflatable cuffs integrally connected together, inserting one of the cuffs into the other of the cuffs including turning one of the cuffs inside-out, placing the cuffs onto the tube including connecting them respectively in fluid communication with said main lumen and said auxiliary lumen means, and sealingly securing both ends of the cuffs to the outer surface of the tube.

2. A method of making a medical double-cuffed retention tube for insertion and retention in a body cavity comprising the steps of forming a tube with main and auxiliary lumens, forming a pair of inflatable cuffs integrally connected together including the step of forming an integral, unitary, double-cuff plastic member including a first cuff of said pair having opposed generally cylindrical end portions, and a second cuff of said pair having opposed cylindrical end portions with one of the end portions of the first cuff connected to one of the end portions of the second cuff, forming a first opening through the sidewall of the tube connecting with the main lumen, forming a second opening through the sidewall of the tube connecting with the auxiliary lumen, inserting one of the cuffs into the other of the cuffs including turning one of the cuffs inside-out, placing the cuffs onto the tube including locating the cuffs so that they are respectively in fluid communication with said first and second openings, and sealingly securing both ends of the cuffs to the outer surface of the tube.

3. The method of claim 1 or 2 wherein the step of forming said cuffs includes molding said cuffs in a common mold from a plastic material.

4. The method of claim 1 wherein the step of forming said cuffs comprises forming an integral, unitary, double-cuff plastic member including a first cuff having opposed generally cylindrical end portions, a second cuff having opposed cylindrical end portions with one of the end portions of the first cuff connected to one of the end portions of the second cuff.

5. The method of claim 1 or 2 wherein the step of forming said cuffs includes forming both of said cuffs from the same plastic extrudate.

6. A method of making a medical double-cuffed retention tube for insertion and retention in a body cavity comprising the steps of forming a tube having a main lumen therethrough and an opening in the sidewall connected with the main lumen, forming a pair of inflatable cuffs integrally connected together, inserting one of the cuffs into the other of the cuffs including turning one of said cuffs inside-out, placing the cuffs onto the tube including connecting the inner cuff to the main lumen through said opening, and sealingly securing both ends of the cuffs to the tube including the steps of inserting a pipe into one end of the tube and through said opening and into the interior of the inner cuff, and flowing sealing material through the pipe and into contact with the tube and one end of the inner cuff.

7. The method of claim 6 wherein said tube and said cuffs are formed of polyvinyl chloride and said sealant is a solvent for polyvinyl chloride.

8. The method of claim 7 wherein said solvent is cyclohexanone.

9. A method of making a double-cuffed medical tube for insertion and retention in a body cavity comprising the steps of providing a plastic tube having a main lumen and auxiliary lumen means, forming a sidewall opening in the tube extending from the outer surface of the tube to the main lumen, forming a pair of plastic inflatable cuffs each having opposed ends for sealingly connecting the cuffs on the tube, placing the cuffs on the tube with one cuff within the other cuff with the inner cuff in fluid communication with said sidewall opening, connecting the outer cuff in fluid communication with said auxiliary lumen means, and sealingly securing the opposed ends of each of the cuffs while they are both on the tube to ther outer surface of the tube including the step of inserting a pipe into one end of the tube and one end of the pipe through said sidewall opening, and flowing a sealing material in the pipe and out said pipe one end to apply the sealing material to one end of the inner cuff to sealingly secure the same to the outer surface of the tube.

10. The method of claim 9 wherein said sealing material is a liquid adhesive.

11. The method of claim 9 wherein said sealing material is a solvent for the plastic materials of the cuffs and the tube.

12. The method of claim 9 or 11 wherein said one end of said pipe extends generally radially from the longitudinal axis of the tube and pipe.

13. The method of claim 9 wherein the step of forming the pair of cuffs comprises forming a unitary double-cuffed plastic member which includes the pair of cuffs integrally connected to each other.

14. A method of making a double-cuffed endotracheal tube comprising the steps of providing a plastic tube having main and auxiliary lumens, forming a first opening in the tube extending between the outer surface of the tube and the main lumen, forming a second opening in the tube extending from the outer surface of the tube to the auxiliary lumen, forming a unitary, plastic, double-cuffed member having first and second spaced inflatable cuffs connected together by an integral intermediate generally tubular portion, and first and second generally tubular end portions at the opposed ends of said member respectively connected to said first and second cuffs, inverting and inserting said first cuff into the interior of said second cuff including folding said intermediate portion back upon itself, positioning the cuffs on the tube with the interior of said first cuff in fluid communication with said first opening and the interior of said second cuff in fluid communication with said second opening, and sealingly securing the folded back intermediate portion and said first and second tubular end portions to the outer surface of the tube.

15. The method of claim 14 wherein said sealingly securing step includes inserting a pipe into the distal end of the main lumen and moving the tip end portion thereof through said first opening, and flowing sealing securing material into the pipe and out the tip end to apply the sealing securing material to said first tubular end portions to seal the same to the outer surface of the tube.

16. The method of claim 14 wherein the double-cuff member is molded in a common mold.

17. The method of claim 14 wherein said first cuff has a small or inflated volume than that of said second cuff.

18. The method of claim 14 or 15 wherein said first tubular end portion is within said second cuff.

19. The method of claim 14 wherein the step of positioning the cuffs on the tube includes locating said first tubular end portion distally of said intermediate tubular end portion and axially between said intermediate tubular end portion and said second tubular end portion.

20. The method of claim 9 or 14 wherein said tube is extruded from plastic and said auxiliary lumen is formed integrally with said tube during the extrusion thereof.

* * * * *